May 13, 1958 O. R. BRISTOW Plant Pat. 1,705
AZALEA PLANT
Filed May 6, 1957
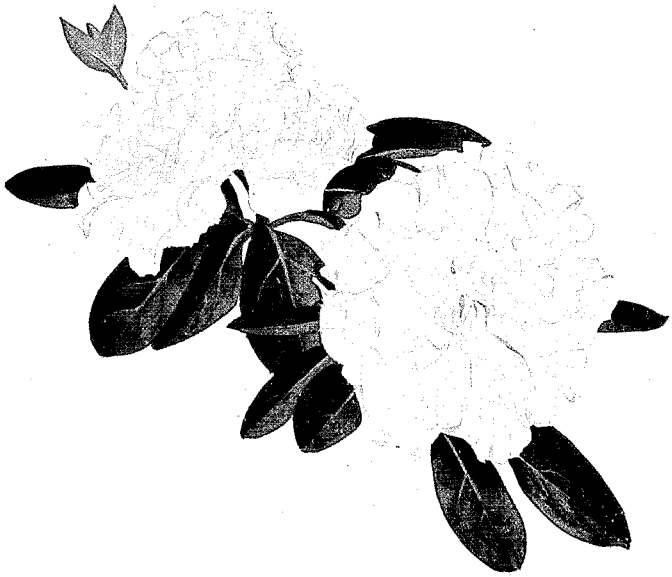
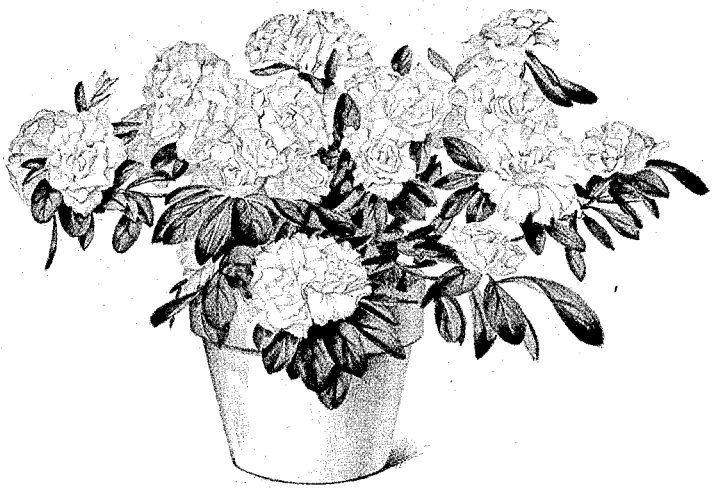
OWEN R. BRISTOW
INVENTOR.
BY Orville R. Seidner
AGENT United States Patent Office Plant Pat. 1,705
Patented May 13, 1958

1,705

AZALEA PLANT

Owen R. Bristow, San Bernardino, Calif., assignor to Mossholder Nursery, Orange County, Calif.

Application May 6, 1957, Serial No. 657,468

1 Claim. (Cl. 47—60)

This invention relates to a distinct and new variety of azalea plant reproduced as a result of deliberate experiments in hybridization carried out at my nursery in San Bernardino, California, the plant being derived from a cross-breeding of unpatented plants numbered 109B and 42 in my breeding records. This particular plant has been given the number 3A for identification purposes.

The distinct and new variety of azalea plant described and claimed herein is to be distinguished over all other varieties, so far as I am aware, in the exceptional commercial value residing in its unusual growing attributes and the outstanding color and longevity of the flowers.

Thus the distinguishing characteristics of this azalea adapt it as an exceptionally good plant for florists. A forced plant of this variety, for example, is in good salable condition for a period of at least 30 days when the buds are ready to open into full bloom. While the buds are opening, they present an unusual aspect of rosebud form which is very striking.

Another distinguishing characteristic is to be found in the luxurious double flower with exceptional lasting quality which results when the bud is fully open, the flower having an outstandingly delicate and enchanting pink color which is particularly good for florists. The lasting quality of the flower, as set forth more specifically below, make this plant a very desirable commodity from the standpoint of the grower or florist and of the purchaser.

Asexual reproduction of this distinct and new variety of azalea was accomplished by me at my nursery in San Bernardino, California, by the known method of removing cuttings from the original hybrid plant which matured from a seedling, and potting the cuttings separately from the donor plant. Subsequent reproductions of the plant in the same manner indicate that the foregoing characteristics, as well as further distinguishing characteristics brought forth in the description below, are permanently fixed, and the accompanying illustration of a forced cutting in bloom shows the prolific blooming and striking color of the flowers.

The following is a detailed specification of the plant and flower, reference being had to the British Horticultural Chart of the British Colour Council for color identification of the flower and filament, and to the Plochere Color System for color identification of the foliage:

*Plant*

Form of plant: Bushy; symmetrical form; height and breadth of 2-year old plants approximately the same with older plants tending to acquire more growth in breadth than height.

Growth habit: Tendency to long branch growth unless properly pinched or pruned; growth rate similar to Kurume type azalea.

Rooting: Roots easily into vigorous rooting system; grows well on its own roots.

Blooming habit: Prolific blooms when forced in glass house; blooms freely outdoors for a long period of time.

Blooming season: Outdoor blooming in southern California from middle of March through April; easily forced for periods from Valentine Day through Easter.

Suitability for forcing: Very good forcing variety.

*Foliage*

Size: Mature leaves average from 1½″ to 2″ long and ¾″ wide. A few large leaves on each plant measure 1″ across.

Quantity: Abundant.

Color: New foliage—Plate #1122 on upperside, and Plate #1123 on underside; old foliage—deep green (not very glossy), Plate #1129 on upperside, and Plate #1130 on underside.

Shape: Oval and slightly pointed (average leaf is somewhat longer than most Belgian Indica varieties).

Texture: Normal.

Edge or margin: Smooth.

Ribs and veins: Normal.

Aspect: Very attractive deep green abundant foliage with growth similar to Belgian Indica.

*Flower*

Size: 2½″ to 3″ across.

Flowers borne: 1 to 3 on each stem.

Quantity of bloom: Abundant.

Continuity: Lasting quality far exceeds any known variety. Most flowers never fall, but remain on the plant 4 to 5 weeks—even after the flowers have dried up.

Petalage:

*Size.*—Large petals average 1½″ to 2″ long and ⅞″ to 1¼″ wide. Small petals average 1″ to 1¼″ long and ½″ to ⅝″ wide.

*Number of petals under normal conditions.*—26 to 30 on each flower. There are 4 rows of petals on each flower; outside or first row in the sepal developed into the calyx with 5 petals; second row has 5 petals also; third and fourth rows have 8 to 10 petals each; center of flower usually has 3 to 8 petaloids.

*Color of bud.*—Tight bud, Plate #533; bud just prior to opening, Plate #523/1 with shades of Plates #523/2 and #523/3 (same as flower).

*Color of open flower.*—Plate #523/1 with shades of Plates #523/2 and #523/3.

*Texture.*—Smooth.

Appearance: When bud is opening it resembles a fully double rose bud; when fully open the flower is completely double.

Shape: Ruffled or frilled edge.

Arrangement: Upright and well balanced.

Persistence: Sets buds regularly every year in southern California; flowers lightly from November to the heavy blooming period in the spring.

*Reproductive organs*

Stamens: Usually none; occasionally 1 to 3 undeveloped stamens about ¼″ long with little or no anther (imperfect stamen and pistil, usually distorted).

Filament: Short; usually less than ¼″ long. Color—creamy white, Plate #663/2.

Styles: Light green, ½″ or less in length when in flower; usually imperfect.

Stigma: Lettuce green.

Ovary: Normal, except slightly undersized.

Having illustrated and described the invention or discovery, what is claimed as new and patentable is:

A distinct and new variety of azalea plant, substantially as illustrated and described hereinabove, and characterized generally by the extended salable period of the forced plant when the buds are ready to open into full bloom, and particularly characterized by rosebud form of the bud while opening and the exceptional lasting quality of the unusual double flower having an outstandingly delicate pink color.

No references cited.